United States Patent [19]

Wood et al.

[11] 4,183,959

[45] Jan. 15, 1980

[54] EMOLLIENT-CONTAINING UREA-BASED BATH BEAD COMPOSITION AND THE PRODUCTION THEREOF

[75] Inventors: Donald C. Wood, Des Plaines; Robert L. McLaughlin, Wilmette, both of Ill.

[73] Assignee: DeSoto, Inc., Des Plaines, Ill.

[21] Appl. No.: 901,855

[22] Filed: May 1, 1978

Related U.S. Application Data

[63] Continuation-in-part of Ser. No. 635,282, Nov. 26, 1975, and Ser. No. 699,982, Jun. 25, 1976, Pat. No. 4,093,745.

[51] Int. Cl.² .................. A61K 7/46; A61K 7/50; C11B 9/00
[52] U.S. Cl. .................. 424/358; 252/522; 424/65; 424/69; 424/76; 424/359; 424/361; 424/363; 424/365
[58] Field of Search .......... 264/7, 13, 14; 424/65, 424/69, 76, 358, 359, 361, 363, 365; 252/522

[56] References Cited

U.S. PATENT DOCUMENTS

| | | | |
|---|---|---|---|
| 1,734,260 | 11/1929 | Lamont | 264/14 |
| 3,196,079 | 7/1965 | Blaustein | 424/69 |
| 3,268,631 | 8/1966 | Price | 264/14 |
| 3,686,373 | 8/1972 | Griesheimer | 264/14 |
| 3,689,678 | 9/1972 | Fox | 424/365 |
| 3,851,065 | 11/1974 | Ludwig | 424/346 |
| 3,952,078 | 4/1976 | Bradley | 264/13 |
| 4,020,156 | 4/1977 | Murray | 424/65 X |
| 4,093,745 | 6/1978 | Wood et al. | 424/358 |

OTHER PUBLICATIONS

Conoco, Alfonic, Ethoxylate Nonionics, Conoco Chemicals, Continental Oil, Houston, Tex. Jan. 1978, brochure, 4 pages.

*Primary Examiner*—Anna P. Fagelson
*Attorney, Agent, or Firm*—Dressler, Goldsmith, Clement, Gordon & Shore, Ltd.

[57] ABSTRACT

Emollient-containing urea bath bead compositions are disclosed in which an oily perfume is present in a low-foaming or nonfoaming system, while minimizing scum formation on the bathtub walls. Also, anticaking particles are associated with the prills in a nonsegregating fashion, and water is included in the materials sprayed on the urea prills so that water soluble dyes can be dissolved in the water and applied to the prills at the same time.

10 Claims, No Drawings

EMOLLIENT-CONTAINING UREA-BASED BATH BEAD COMPOSITION AND THE PRODUCTION THEREOF

This invention is a continuation-in-part of our prior applications, Ser. Nos. 635,282 and 699,982 (now U.S. Pat. No. 4,093,745) filed Nov. 26, 1975 and June 25, 1976, respectively.

The present invention relates to perfumed emollient-containing urea bath beads which minimize or avoid the deposition of an oily scum on the walls of bathtubs in which they are used. The invention includes the production of emollient-containing urea beads in the form of a free flowing powder including particles of an anti-caking agent associated with the beads in a nonsegregating fashion. The invention includes improved procedures enabling the use of continuous production equipment.

In this invention, the urea beads, sometimes termed prills, are tumbled with a mixture of 0.2% to 2.0% of an oily perfume and 0.3% to 2.0% of a water soluble polyalkylene ether emollient to cause the perfume and the emollient to be distributed over the beads. All proportions herein are by weight unless otherwise stated, and the above proportions are based on the weight of the urea prills. The use of the selected emollient provides bath beads which keep the perfume from depositing on the walls of the bathtub even though little or no foam is produced in the bath water.

The urea prills are preferably dyed with a water soluble dye to provide an attractive coloration for the beads and for the bathwater in which the beads are dissolved. It has been found that water can be used in the material applied to the urea prills in an amount of from 5–20% of the total weight of perfume and emollient to provide a water-containing liquid spray in which the desired dye can be dissolved. In this way the separate step of tumbling the prills with powdered dye can be eliminated, and this is helpful to the use of continuous processing where the number of points at which extraneous materials are brought into the process is desirably minimized.

Another aspect of this invention is the application of finely divided particles of anticaking agent to the urea prills, usually after the perfume and emollient have been distributed over the surface of the prills, but before the prills are dry enough to be free flowing, in order that the anticaking particles will adhere to the beads in a nonsegregating fashion. Using corn starch, this same result can be obtained in an even more effective manner.

The urea beads or prills are readily available in commerce and their characteristics and use in bath bead compositions is more fully discussed in our prior applications referred to hereinbefore, the disclosures of which are hereby incorporated by reference.

The need to perfume compositions intended to be used in the bath is self-evident, but when oily perfumes are used in a low-foaming or nonfoaming bath composition, these oils form a scum on the walls of the bathtub and this is undesirable. Perfumes, as a class, are oily materials and are illustrated by rose oil, honeysuckle oil, lilac oil, lemon oil, and the like.

The water soluble polyalkylene ether emollients can be of various types, but it is preferred to employ aliphatic alcohols having from 8–22 carbon atoms, and more preferably, straight chain alkanols containing from 9–16 carbon atoms, which are adducted with from 6 to 12 mols of ethylene oxide per mol of alcohol. These have a hydrocarbon portion of sufficient length to provide an emollient function, and they possess sufficient ethylene oxide units to provide a surfactant function which keeps the oily perfume from adhering to the bathtub walls.

As will be evident, the oily perfume and the polyalkylene ether emollient are used in small amount, and other materials which may optionally be added are also used in small amount so that the urea beads will constitute at least about 92% of the composition, and more preferably, at least about 95% of the weight of the composition.

Water soluble dyes suitable for the present purposes are food, drug and cosmetic dyes or drug and cosmetic dyes, these being normally used as color additives in beverages, confections, and/or pharmaceuticals. The dyes can be of any desired color, in finely divided solid or crystalline state, and can be selected from nitro, monoazo, diazo, phthalocyanine, quinoline, xanthene, triacrylmethane, indigoid, vegetable dyes, and the like. Blue and green dyes are preferred as being generally more attractive for the present purposes. Illustrative suitable dye is FD&C Blue No. 1, i.e., a color additive which is principally the disodium salt of ethyl (4-[para-[ethyl(metha-sulfobenzyl)amino]-alpha-(ortho-sulfophenyl)benzylidene)-2,5-cyclohexadien-1-ylidene] (meta-sulfobenzyl) ammonium hydroxide inner salt with smaller amounts of the isomeric disodium salts of ethyl[4-(para-[ethyl(para-sulfobenzyl)amino]-alpha-(orthosulfophenyl)benzylidene)-2,5-cyclohexadiene-1-ylidene] (parasulfobenzyl) ammonium hydroxide inner salt and ethyl [4-(paraethyl(ortho-sulfobenzyl)amino]-alpha-(ortho-sulfophenyl)benzylidene)-2,5-cyclohexadien-1-ylidene] (ortho-sulfobenzyl) ammonium hydroxide inner salt.

From the standpoint of producing a dyed bead composition, it is desirable to be able to apply the perfumes, emollients and dyes in a single application step. For this purpose it has been found, that from 5% to 20% of the total weight of perfume and emollients can be constituted by water, and the dye which is desired to be applied can be dissolved in water so that the liquid mixture of oily dye, emollients and dye-containing water can be sprayed onto the urea prills with all of these components being absorbed simultaneously.

The initial mixture which includes the urea beads or prills and the oily liquid mixture, including the emollient, forms an initially sticky mass.

Urea prills normally have a relatively dull surface which becomes shiny when the oily emollient is distributed thereon, and this shine can be used to measure the uniformity of distribution of the oily liquid. Thus, after addition of the emollient, the combination is agitated (tumbled) until the prills present a substantially uniform shiny appearance. Preferably, the prill-and-emollient combination is tumbled or otherwise agitated until the oily materials are at least partially absorbed or adsorbed and individual emollient-bearing prills begin to move relative to one another or separate from one another.

It is important that the bath beads include a particulate anticaking agent which is uniformly distributed and which does not segregate on storage. For this purpose, the sticky surfaces of the emollient-bearing prills are coated with the particles of anticaking agent having a particle size which is substantially less than the size of the urea prills. The coating operation can be carried out in a tumbling barrel, a rotating pan mixer, an inclined open-ended rotary drum, by passing the prills through a fluidized bed of the anticaking agent, or in any other convenient manner. The powdered anticaking agent should be added to the emollient-bearing prills after the emollient thereon has been substantially distributed because, otherwise, the anticaking powder will absorb emollient yielding lumps which interfere with the uniform distribution of emollient. If the emollient-bearing prills are agitated without addition of anticaking powder, the emollient will be taken up by the prills to form a free-flowing powder, and it is now too late to add the powdered material since it will not associate with the prills and the mixture segregates on storage.

Continued agitation after addition of the anticaking powder permits the absorption or adsorption of the oily liquid to continue until a free-flowing particulate mixture is obtained. The finely divided anticaking particles remain associated with the urea prills even though there is no longer enough oily liquid on the surface to cause these prills to stick together.

The average particle size of the anticaking particles is preferably up to about ¼th the average diameter of the urea prills, and is more preferably less than ⅛th its diameter.

The anticaking agents which may be used to prevent sticking as a result of water absorption include finely divided modified proteins, water soluble polysaccharides such as corn-starch and the like, natural gums, hydrophobic starch, hydrophylic starch, magnesium stearate, colloidal silicon dioxide, tricalcium phosphate and sulfonated formaldehyde condensates. Salts which absorb moisture by forming hydrates and which do not induce significant alkalinity in the small proportions utilized can also be used, for example, anhydrous magnesium sulfate. Anticaking agents are well known, per se, and their use is itself conventional. They are used herein in an amount of 0.05% to 2%, based on the weight of the urea prills.

To stabilize the pH of the bath water, powdered buffering agents such as citric acid, fumaric acid, tartaric acid, and the like, can also be adhered onto the emollient-bearing prills together with the powdered anticaking agent. Similarly, powdered preservatives such as the lower alkanol esters of parahydroxybenzoic acid, e.g., methyl paraben, propyl paraben, mixtures thereof, and the like, can be incorporated into the bath bead composition when practicing the present invention. Similarly germicides like 2.4,4'-trichloro-2'-hydroxy-diphenyl ether can be used in an amount of 0.1% to 3% of the weight of the beads.

Most of the compositions described in our prior applications referred to earlier produce a substantial amount of foaming, so the problem of perfume separation was not a factor.

The invention is illustrated in the following example.

EXAMPLE

Urea prills (passes No. 6 Sieve and retained on No. 20 Sieve) (U.S. Sieve Series)—98.39
Perfume (honeysuckle oil)—0.5
Emollient (Alfonic 1412-60)—0.5
Water—0.1
Dye (Blue No. 1)—0.01
Anticaking agent (corn starch, water and oil absorptive) [finely divided powder]—0.5

A liquid mixture of the perfume and emollient is formed and the water containing the dissolved dye is added thereto. The resulting dye-containing mixture is sprayed on the urea prills tumbling in a tube which is inclined to an angle of 5° providing a dwell time of 10 minutes.

The product falling out of the tube is sticky and the anticaking powder is distributed upon it. This mixture is tumbled in a second tube for 1 minute to provide a free flowing dyed bead product having the anticaking powder adhered to the beads in a manner resisting segregation on storage.

Corn starch is usually effective since it has the capacity to absorb both water and oil, and both are present. Curiously, and using corn starch, the starch can be added to the urea beads first and the remaining materials sprayed on as a second step. The result is a free flowing bead composition which is produced with reduced mixing time. Thus, corn starch represents a special case where the otherside preferred procedure is not needed. Thus, an equivalent result in the present example can be obtained by dusting the corn starch onto the urea prills, and then spraying the mixture of the remaining components onto the dusted urea beads in a tumbler using a dwell time of 2 minutes to produce a free flowing bead composition directly.

We claim:

1. An emollient-containing urea bath bead composition which produces little or no foam in the bath water comprising urea prills having absorbed therein from 0.2% to 2.0% of an oily perfume and from 0.3% to 2.0% of a water soluble polyalkylene ether emollient constituted by aliphatic alcohols having from 8–22 carbon atoms adducted with from 6–12 mols of ethylene oxide per mol of alcohol, based on the weight of the urea prills, whereby the formation of an oily scum when the bath bead composition is dissolved in water is minimized.

2. A bath bead composition as recited in claim 1 in which said urea prills are dyed with a water soluble dye.

3. A bath bead composition as recited in claim 1 in which said alcohols are straight chain alkanols containing from 9–16 carbon atoms.

4. A bath bead composition as recited in claim 1 in which said urea prills constitute at least 92% of the composition.

5. A bath bead composition as recited in claim 4 in which finely divided particles of anticaking agent are adhered to said urea prills.

6. A bath bead composition as recited in claim 5 in which said anticaking agent is corn starch.

7. A method of producing a bath bead composition as recited in claim 5 comprising spraying a liquid mixture of said oily perfume and said emollient onto said urea prills, agitating the mixture so-provided to distribute said perfume and said emollient over the surface of said prills, distributing finely divided particles of anticaking agent onto said prills while the surface thereof is sticky with the materials distributed thereon, and then continuing to agitate the mixture until the prills are free flowing with the particles of anticaking agent adhered thereto.

8. A method as recited in claim 7 in which said liquid mixture of perfume and emollient contains from 5% to 20% of water, based on the total weight of perfume and emollient, and a water soluble dye is dissolved in said water.

9. A method of producing a bath bead composition as recited in claim 2 comprising spraying a liquid mixture of said oily perfume and said emollient onto said urea prills, said liquid mixture containing 5% to 20% of water, based on the total weight of perfume and emollient, and said water having a water soluble dye dissolved therein, and tumbling said sprayed urea prills to distribute the liquid mixture over the surface of said prills and to cause said prills to be dyed by said dye.

10. A method as recited in claim 9 in which corn starch is distributed over said urea prills before the liquid mixture of oily perfume, emollient, water and dye is sprayed thereon.

* * * * *